(12) United States Patent
Khatri et al.

(10) Patent No.: US 9,434,668 B1
(45) Date of Patent: Sep. 6, 2016

(54) PROCESS FOR THE PRODUCTION OF TERTIARY BUTYL PHENOLS

(71) Applicant: Council of Scientific and Industrial Research, New Delhi (IN)

(72) Inventors: Praveen Kumar Khatri, Dehradun (IN); Suman Lata Jain, Dehradun (IN); Indrajit Kumar Ghosh, Dehradun (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 14/955,607

(22) Filed: Dec. 1, 2015

(30) Foreign Application Priority Data

Apr. 9, 2015 (IN) .............................. 992/DEL/2015

(51) Int. Cl.
*C07C 37/00* (2006.01)
*C07C 37/11* (2006.01)
(52) U.S. Cl.
CPC ...................................... *C07C 37/11* (2013.01)
(58) Field of Classification Search
CPC ...................................................... C07C 37/11
USPC ....................................................... 568/785
See application file for complete search history.

(56) References Cited

U.S. PATENT DOCUMENTS

| | | | |
|---|---|---|---|
| 4,532,368 A | 7/1985 | Swanson et al. | |
| 5,399,786 A | 3/1995 | Queiroz et al. | |
| 5,475,178 A | 12/1995 | Del Rossi et al. | |
| 6,204,424 B1 | 3/2001 | Yadav et al. | |

FOREIGN PATENT DOCUMENTS

| | | |
|---|---|---|
| WO | WO-2011/069052 | 6/2011 |
| WO | WO-2011/069052 A2 | 6/2011 |
| WO | WO-2011/069052 A3 | 6/2011 |

OTHER PUBLICATIONS

Dumitriu, Emil, et al., "Effects of channel structures and acid properties of large-pore zeolites in the liquid-phase *tert-* butylation of phenol", *Journal of Catalysis, 218*, (2003), 249-257.

Shen, Hao-Yu, et al,, "Comparative studies on alkylation of phenol with *tert*-butyl alcohol in the presence of liquid or solid acid catalysts in ionic liquids". *Journal of Molecular Catalysis A: Chemical 212*, (2004), 301-308.

Shinde, Ajit B., et al., "*tert*-Butylation of phenols using *tert*-butyl alcohol in the presence of FeCl$_3$-modified montmorillonite K10", *Applied Catalysis A: General, 276*, (2004), 5-8.

*Primary Examiner* — Sikarl Witherspoon
(74) *Attorney, Agent, or Firm* — Schwegman, Lundberg & Woessner, P.A.

(57) ABSTRACT

The present invention relates to an improved process for the selective alkylation of phenols by reacting it with methyl tertiary butyl ether (MTBE) using polymer supported carbon composite acidic catalyst under mild to moderate conditions at atmospheric pressure. The process is economically viable since the catalyst regenerated after the initial reaction on further use gives the para tertiary butyl phenol (PTBP) in high yield.

11 Claims, No Drawings

PROCESS FOR THE PRODUCTION OF TERTIARY BUTYL PHENOLS

CLAIM OF PRIORITY

This application claims the benefit of priority of India Patent Application No. 992/DEL/2015, filed on 9 Apr. 2015, the benefit of priority of which is claimed hereby, and which is incorporated by reference herein in its entirety.

FIELD OF INVENTION

The present invention relates to an improved process for the selective production of para tertiary butyl phenol. More particularly the present invention relates to an improved process for selective phenol alkylation with methyl tertiary butyl ether.

BACKGROUND OF THE INVENTION

Para tertiary butyl phenol is a stable and readily biodegradable chemical which is being widely used as an intermediate for phenol resins and polycarbonate resins. It is also used as a raw material for construction elements and floors in buildings.

Additionally, certain tert-butyl phenols are useful as fragrance or flavor compounds and may be used in a wide variety of household, personal care, and industrial items, such as perfumes, cleansers, or detergents. Conventional processes for producing tert.-butyl phenols from an isobutylene-containing $C_4$ raffinate stream typically involve introducing methanol, or another alcohol, into the $C_4$ stream to react and produce alkyl tertiary butyl ether intermediate that is further decomposed to make high-purity isobutylene, which can then be reacted with phenol to produce the t-butyl phenol. The additional step of adding methanol significantly increases the costs of producing t-butyl phenols and creates another undesirable byproduct. Besides the additional expense, the additional byproducts are unattractive for environmental reasons. Isobutylene may also be produced by isobutanol dehydration. However, in this case an impure product may form which, when used for alkylating phenols, leads to the formation of phenol by-products, such as derivatives having a secondary butyl substitute.

U.S. Pat. No. 4,532,368 discloses a process for the production of meta and para-alkylphenols from phenol and olefins in the presence of silicalites and ZSM-5 as catalyst at a temperature of 200° C. to 500° C.

U.S. Pat. No. 5,475,178 discloses a process for the alkylation of phenol with olefins using phosphotungsticacid supported on MCM-41 at a temperature range of 0° C. to 500° C. and at a pressure ranging from 0.2 to 250 atmospheres.

U.S. Pat. No. 5,399,786 discloses a process for the preparation p-tert butyl phenol by the reaction of phenol with alkyl tert-butyl ether in the presence of a protonated strong acid type catalyst in the temperature range of 60° C. to 130° C. and pressure ranging between atmospheric pressure to 5 kg/cm$^2$.

U.S. Pat. No. 6,204,424 discloses a process for the alkylation of phenol with tert.-butyl ether and benzyl chloride in the presence of solid acid catalysts such as sulphated oxides of different metals such as Zr, Ti, Fe, Al, Sn and Bi.

Further, there have been proposed a process based on reaction of phenol with an isobutylene oligomer in the presence of Bronsted acid such as sulfuric acid, hydrofluoric acid, etc. and a process based on the reaction using ion exchange resins, etc. However, these prior art processes have certain disadvantages and have not been used as an industrial scale process. The use of Bronsted acids such as sulfuric acid, hydrofluoric acid, etc as catalysts causes serious corrosion problems at high temperature and it is difficult to carry out the reaction at a temperature higher than 120° C. When the reaction temperature is lowered, more by-products are produced and the yield of the desired 4-TBP is lowered. Furthermore, the use of these corrosive acids is undesirable from environmental points of view.

In the prior art process where ion exchange resins are used, there is neither corrosion of the reaction apparatus nor environmental pollution, but the reaction must be carried out at a reaction temperature of 110° C. or less, because the physical strength of the ion exchange resins is lowered at a high temperature and therefore, the yield of the desired 4-TBP is disadvantageously lowered.

Patent DD 87-311221 (Dec. 24, 1987) describes a process for the preparation of mono, bi-tri-tert-alkylated phenol derivatives using n-alkyl-tert-alkylethers. The process requires equimolar amounts of phenol and acid which generate corrosion problems due to high temperature.

U.S. Pat. No. 5,399,786 describes the preparation of tert.-butylphenols by the reaction of phenol with alkyl-tert-butyl ether instead of using pure isobutylene. The advantage of the process is mainly with the increased yield of the product from 88.7% (basic process) to 94.8%.

World patent (WO 2011069052 A3) disclosed a process for the production of various t-butyl phenols, such as 2,6-di-tert-butyl phenol and ortho-tert-butyl phenol, by selectively reacting phenol or a substituted phenol with an isobutylene-containing C4 raffinate stream.

A number of research papers have been published on the synthesis of alkyl phenol via alkylation of phenol. Samant and co-workers have reported (Appl. Catal. A, 2004, 276, 5) a liquid phase tert-butylation of phenol in the presence of k-10 clay and FeCl$_3$/k-10 clay as catalysts. The process gave 100% conversion with 62.0% and 66.8% selectivity for p-tert-butylphenol respectively.

V. Hules reported (J. Catal, 2003, 218, 249) 52.7% conversion with 23.0% selectivity for p-tert-butylphenol using USY as catalyst, 54.2% conversion with 80.3% selectivity for p-tert-butylphenol using Zeolite-β, 28.8% conversion with 49.1% selectivity for p-tert-butylphenol using Mordenite, 12.6% conversion with 79.5% selectivity for p-tert-butylphenol using HZSM-5, and 31.5% conversion with 99.3% selectivity for p-tert-butylphenol using H-β as the solid acid catalyst in presence of ionic liquids such as [bmim]PF6, [omim]BF4 and [hmim]BF4.

Y. Shen and co-workers have reported (J. Mol. Catal. A 2004, 212, 301) 44.8% conversion with 49.0% selectivity for p-tert-butylphenol with tungstophosphoricacid supported onto MCM-41 as catalyst.

Of all the reactions described in the art, has certain drawbacks and provided lower yield of the desired p-tert. butyl phenol. The present invention has its advantages in using MTBE directly that provides insitu generation of isobutylene by cracking and providing more than 99% conversion with higher selectivity for p-tert butylphenol.

OBJECTIVE OF THE PRESENT INVESTIGATION

An object of the present invention is to eliminate the disadvantages of the prior art processes and to provide a one-step process for producing 4-TBPs in high yields.

Another object of the present invention is to provide a process for producing 4-TBP in high yield by using methyl tertiary butyl ether directly without any of additional steps of methanol addition.

It is an object of the present invention to provide a high yielding and selective process for the tert-butylation of phenol in liquid phase.

It is a further object of the present invention to provide a process for the tert-butylation of phenol in liquid phase with catalyst regeneration.

It is yet another object of the invention to provide a process for the tert-butylation of phenol in liquid phase with comparable selectivity in liquid phase by the use of regenerated catalyst.

Other object of the present invention is to provide a process based on the use of a specific catalyst without causing any corrosion of reaction apparatus.

Still further object of the present invention is to provide a process for producing the desired 4-TBP in high yield by using recyclable heterogeneous catalyst.

Still further object of the present invention is to provide a process for producing the desired 4-TBP in high yield by using a catalyst that can be worked at a higher reaction temperature.

SUMMARY OF THE PRESENT INVENTION

Accordingly the present invention provides an improved process for production of tertiary butyl phenols by selective alkylation of phenols by reacting said phenols with methyl tertiary butyl ether (MTBE) in the molar ratio 1:1 to 1:5 using sulfonic acid functionalized polymer supported carbon composite solid acid catalyst in 0.5-10 wt % with respect to total weight of phenol and MTBE, under the temperature in the range of 100-160° C. at atmospheric pressure for 1 to 5 h, provided more than 99% conversion with 70-80% selectivity for the p-tert. butyl phenol with the facile recovery and recycling of the recovered catalyst for at least seven runs.

In an embodiment of present invention, the phenol to MTBE molar ratio is in the range 1:1 to 1.5:1, preferably 1:1 to 1.2:1.

In another embodiment of present invention, the solid acid catalyst was used in 2 to 5 wt % with respect to total weight of phenol and MTBE.

In yet another embodiment of present invention, the reaction is carried out at a temperature range of 110-150° C., preferably at 140° C.

In still another embodiment of present invention, the reaction results in more than 99% conversion of MTBE with the selectivity for desired PTBP in the range of 70-80%, particularly in 75-80%.

In still another embodiment of present invention, the solid acid catalyst was easily recovered by simple filtration and subsequently used for recycling experiments.

In still another embodiment of present invention, the recovered catalyst showed consistent catalytic activity at least for seven runs.

In still another embodiment of present invention, the MTBE is directly reacted with phenol, without requiring an intermediate step of forming alkyl-tert-butyl ether.

DETAILED DESCRIPTION OF THE INVENTION

The present invention relates to an improved process for the tert-butylation of phenol in liquid phase under mild to moderate (140° C., 1 atmospheric pressure) conditions with more than 99% conversion and around 70-80% selectivity for p-tert-butylphenol in the presence of polymer matrix impregnated carbon composite acidic catalyst containing sulfonic acid groups. The advantage of the process lies in the simple regeneration of the catalyst. The regenerated catalyst gave comparable yield and selectivity for p-tert-butylphenol for 7 cycles. The present invention is therefore economically viable.

The alkylation reaction is carried out in a 100 ml stainless steel high pressure parr autoclave equipped with four bladed pitched impeller for agitation.

Phenol and MTBE is taken in a molar ratio ranging from 1:1 to 1:1.5 followed by the addition of catalyst in the amount of 2-5 wt % with respect to total weight of both reactants. The resultant mixture is heated in the temperature range of 110° C. to 150° C. for 1 h to 3 h.

For alkylation of phenol with MTBE as a source of isobutylene, the obtained products o-tert.-butyl phenol (OTBP), p-tert-butyl phenol (PTBP) and 2,4-di-tert-butyl phenol (2,4-DTBP) were identified on gas chromatograph (Varian CP 3800) and product identification was done by comparison with authentic samples as well as by a combined gas chromatography-mass spectrometry. Further, the isomers were separated by HPLC (Shimadzu) using Nucleosil $C_{18}$ column and identified by $^1H$ NMR spectroscopy. The conversion of phenol under optimized reaction conditions was found to be 99% with the 80% selectivity for PTBP.

Preparation of the polymer impregnated-$SO_3H$ functionalized carbon composite

Polymer impregnated —$SO_3H$ containing carbon composite (P—C—$SO_3H$) was synthesized by the pyrolysis of a polymer matrix impregnated with D-glucose and followed by its sulfonation with $H_2SO_4$. In a typical experiment, a solution of glucose (2.0 g) in 3 ml of deionized water was added with a minute amount of $H_2SO_4$ (2 drops) and the resulting mixture was slowly added to a pre dried Merrifield polymer resin (2 g) with magnetic stirring. After complete addition of glucose solution, the resulting mixture was dried at 110-120° C. for overnight. Thus obtained black material was crushed to powder and then calcined under dry nitrogen at 300° C. for 1 h in a muffle furnace. The resulting black residue was further sulfonated by using concentrated sulfuric acid (1 g. solid/20 ml $H_2SO_4$) at 160° C. for overnight under dry nitrogen atmosphere. The mixture was diluted with plenty of distilled water and the black material so obtained was collected by filtration, washed several times with hot distilled water of 80° C. until impurities like sulfate ions were no longer detected in the wash water. The resulting black solid (P—C—$SO_3H$) was dried in an oven at 80° C. under vacuum for 5 h and subsequently used for the alkylation of phenol with MTBE.

Following are the examples given to further illustrate the invention and should not be construed to limit the scope of the present invention Example 1

A 100 ml stainless steel parr autoclave was packed with phenol (7.058 g, 75 mmol), MTBE (4.407 g, 50 mmol) and catalyst in 5 wt %. with respect to total weight of reactants. The resulting mixture was heated at 140° C. for 2 h at atmospheric pressure. After completion, the reactor was cooled to room temperature and the heterogeneous catalyst was filtered by simple filtration. The resulting mixture was diluted with acetonitrile and subjected to GC analysis. Gas chromatography analysis of the reaction product revealed that 79% of PTBP was obtained with more than 99% conversion with respect to limiting reactant MTBE. Composition of alkylated phenols in reaction mixture is shown in Table 1

TABLE 1

| Composition of alkylated phenols | |
|---|---|
| Butylated Phenols | Mol % |
| OTBP | 5 |
| PTBP | 79 |
| 2,6-DTBP | — |
| 2,4-DTBP | 16 |

Example 2

A 100 ml stainless steel parr autoclave was packed with phenol (6.21 g, 66 mmol), MTBE (5.28 g, 60 mmol) and 5 wt % of heterogeneous catalyst. The resulting mixture was heated at 140° C. for 2 h at atmospheric pressure. After completion, the reactor was cooled to room temperature and the catalyst was collected by simple filtration. The resulting mixture was diluted with acetonitrile and subjected to GC analysis. The results obtained indicated that 78% of PTBP was obtained with more than 99% conversion with respect to limiting reactant MTBE. Composition of alkylated phenols in reaction product is shown in Table 2

TABLE 2

| Composition of alkylated phenols | |
|---|---|
| Butylated Phenols | Mol % |
| OTBP | 5 |
| PTBP | 78 |
| 2,6-DTBP | — |
| 2,4-DTBP | 17 |

Example 3

A 100 ml stainless steel parr autoclave was packed with phenol (6.21 g, 66 mmol), MTBE (5.28 g, 60 mmol) and 5 wt % of heterogeneous catalyst. The resulting mixture was heated at 130° C. for 2 h at atmospheric pressure. After completion, the reactor was cooled to room temperature and the catalyst was collected by simple filtration. The resulting mixture was diluted with acetonitrile and subjected to GC analysis. Gas chromatography analysis of the reaction product revealed that the 52% of PTBP was obtained with more than 99% conversion with respect to limiting reactant MTBE. On decreasing the temperature from 140° C. to 130° C., the selectivity of PTBP was found to be decreased. Composition of alkylated phenols in reaction product is shown in Table 3.

TABLE 3

| Composition of alkylated phenols | |
|---|---|
| Butylated Phenols | Mol % |
| OTBP | 17 |
| PTBP | 52 |

TABLE 3-continued

| Composition of alkylated phenols | |
|---|---|
| Butylated Phenols | Mol % |
| 2,6-DTBP | — |
| 2,4-DTBP | 31 |

Example 4

A mixture of phenol (6.21 g, 66 mmol) and MTBE (5.28 g, 60 mmol) was charged into a 100 ml stainless steel parr autoclave followed by addition of desired amount of catalyst (5% wt). The resulting mixture was heated at 120° C. for 2 hours at atmospheric pressure. After desired run time of reaction, the reactor was cooled to room temperature. Catalyst was filtered by simple and easy filtration and mixture was extracted with acetonitrile. Gas chromatography analysis of the reaction product revealed that 44% of PTBP was obtained with more than 99% conversion with respect to limiting reactant MTBE. Composition of alkylated phenols in reaction product is shown in Table 4

TABLE 4

| Composition of alkylated phenols | |
|---|---|
| Butylated Phenols | % by mole |
| OTBP | 18 |
| PTBP | 44 |
| 2,6-DTBP | traces |
| 2,4-DTBP | 38 |

Example 5

A 100 ml stainless steel parr autoclave was charged with phenol (6.21 g, 66 mmol), MTBE (5.28 g, 60 mmol) and 5 wt % of catalyst. The resulting mixture was heated at 150° C. for 2 hours at atmospheric pressure. After completion, the reactor was cooled to room temperature and the catalyst was collected by simple filtration. The resulting mixture was diluted with acetonitrile and subjected to GC analysis. Gas chromatography analysis of the reaction product revealed that the selectivity for the PTBP was 80% with more than 99% conversion with respect to limiting reactant MTBE. Temperature rise from 140° C. to 150° C. did not show any noticeable improvement in selectivity of PTBP. Composition of alkylated phenols in reaction product is shown in Table 5

TABLE 5

| Composition of alkylated phenols | |
|---|---|
| Butylated Phenols | Mol % |
| OTBP | 5 |
| PTBP | 80 |
| 2,6-DTBP | — |
| 2,4-DTBP | 13 |

Example 6

A 100 ml stainless steel parr autoclave was charged with phenol (6.21 g, 66 mmol), MTBE (5.28 g, 60 mmol) and 3 wt % of catalyst. The resulting mixture was heated at 140°

C. for 2 hours at atmospheric pressure. After completion, the reactor was cooled to room temperature and the catalyst was collected by simple filtration. The resulting mixture was diluted with acetonitrile and subjected to GC analysis. Gas chromatography analysis of the reaction product revealed that the selectivity for PTBP was 68% with more than 99% conversion with respect to limiting reactant MTBE. By reducing the amount of the catalyst, the selectivity for the PTBP synthesis was decreased significantly. Composition of alkylated phenols in reaction product is shown in Table 6

TABLE 6

| Composition of alkylated phenols | |
|---|---|
| Butylated Phenols | Mol % |
| OTBP | 5.5 |
| PTBP | 68 |
| 2,6-DTBP | — |
| 2,4-DTBP | 26.5 |

Example 7

Recycling of the Recovered Catalyst

A 100 ml stainless steel parr autoclave was charged with phenol (6.21 g, 66 mmol), MTBE (5.28 g, 60 mmol) and 5 wt % of recovered catalyst. The resulting mixture was heated at 140° C. for 2 h at atmospheric pressure. After completion, the reactor was cooled to room temperature and the catalyst was collected by simple filtration. The resulting mixture was diluted with acetonitrile and subjected to GC analysis. Gas chromatography analysis of the reaction product revealed that the selectivity for PTBP was 79% with more than 99% conversion with respect to limiting reactant MTBE. The recovered catalyst was reused for subsequent seven runs. The results of recycling experiments are summarized in Table 7.

TABLE 7

| Results of recycling of the catalyst | |
|---|---|
| Run | PTBP yield (%) |
| 1 | 79 |
| 2 | 79 |
| 3 | 78 |
| 4 | 78 |
| 5 | 78 |
| 6 | 78 |
| 7 | 78 |

Advantages of the Present Investigation

The present process has the following advantages, as compared with the conventional processes for producing PTBP in an industrial scale.

1. Methyl tertiary butyl ether (MTBE) and phenol, both being liquefied are used as raw materials.
2. The desired PTBP can be obtained in one step in high yield without using any isomerization step.
3. A polymer supported carbon composite containing —$SO_3H$ groups is used as catalyst and the reaction is carried out by solid-liquid contact, no neutralization and water washing steps are required.
4. The developed catalyst is heterogeneous in nature and is easily recovered by simple filtration and reused for at least seven recycling experiments.
5. There is no fear of corrosion of the reaction apparatus.
6. Since the MTBE is used as a source isobutylene oligomer, the heat of reaction is small, and the reaction temperature can be readily controlled without using any solvent.

What is claimed is:

1. An improved process for production of tertiary butyl phenols by selective alkylation of phenols by reacting said phenols with methyl tertiary butyl ether (MTBE) in the molar ratio 1:1 to 1:5 using sulfonic acid functionalized polymer supported carbon composite solid acid catalyst in 0.5-10 wt % with respect to total weight of phenol and MTBE, under the temperature in the range of 100-160° C. at atmospheric pressure for 1 to 5 h, provided more than 99% conversion with 70-80% selectivity for the p-tert. butyl phenol with the facile recovery and recycling of the recovered catalyst for at least seven runs.

2. The process as claimed in claim 1, wherein phenol to MTBE molar ratio is in the range 1:1 to 1.5:1.

3. The process as claimed in claim 1, wherein the solid acid catalyst was used in 2 to 5 wt % with respect to total weight of phenol and MTBE.

4. The process as claimed in claim 1, wherein the reaction is carried out at a temperature range of 110-150° C.

5. The process as claimed in claim 1, wherein, the reaction results in more than 99% conversion of MTBE with the selectivity for desired PTBP in the range of 70-80%.

6. The process as claimed in claim 1, wherein the solid acid catalyst was easily recovered by simple filtration and subsequently used for recycling experiments.

7. The process as claimed in claim 1, wherein the recovered catalyst showed consistent catalytic activity at least for seven runs.

8. The process as claimed in claim 1 wherein the MTBE is directly reacted with phenol, without requiring an intermediate step of forming alkyl-tert-butyl ether.

9. The process as claimed in claim 2, wherein phenol to MTBE molar ratio is in the range 1:1 to 1.2:1.

10. The process as claimed in claim 4, wherein the reaction is carried out at 140° C.

11. The process as claimed in claim 5, wherein the reaction results in more than 99% conversion of MTBE with the selectivity for desired PTBP in the range of 75-80%.

* * * * *